US011033601B2

(12) United States Patent
Johnson et al.

(10) Patent No.: US 11,033,601 B2
(45) Date of Patent: Jun. 15, 2021

(54) SELECTIVE INHIBITION OF V1B FOR TREATING FATTY LIVER

(71) Applicant: The Regents of the University of Colorado, Denver, CO (US)

(72) Inventors: Richard J. Johnson, Denver, CO (US); Miguel A. Lanaspa Garcia, Denver, CO (US); Thomas Jensen, Denver, CO (US)

(73) Assignee: The Regents of the University of Colorado, a body corporate, Denver, CO (US)

(*) Notice: Subject to any disclaimer, the term of this patent is extended or adjusted under 35 U.S.C. 154(b) by 0 days.

(21) Appl. No.: 16/131,410

(22) Filed: Sep. 14, 2018

(65) Prior Publication Data

US 2019/0083568 A1 Mar. 21, 2019

Related U.S. Application Data

(60) Provisional application No. 62/558,555, filed on Sep. 14, 2017.

(51) Int. Cl.
*A61K 31/5377* (2006.01)
*A61K 31/404* (2006.01)
*A61K 45/06* (2006.01)
*A61K 38/095* (2019.01)

(52) U.S. Cl.
CPC .......... *A61K 38/095* (2019.01); *A61K 31/404* (2013.01); *A61K 31/5377* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 8,148,319 B2 | 4/2012 | Wisniewski et al. | |
| 8,222,202 B2 | 7/2012 | Laporte et al. | |
| 8,431,567 B2 | 4/2013 | Geneste et al. | |
| 8,461,152 B2 | 6/2013 | Schnider | |
| 8,546,401 B2 | 10/2013 | Braje et al. | |
| 8,580,842 B2 | 11/2013 | Lubisch et al. | |
| 8,703,774 B2 | 4/2014 | Netz et al. | |
| 8,703,775 B2 | 4/2014 | Oost et al. | |
| 2008/0275026 A1 | 11/2008 | Hudson et al. | |
| 2009/0181909 A1 | 7/2009 | Purschke et al. | |
| 2009/0182022 A1* | 7/2009 | Rongen ............... A61K 31/202 | 514/365 |
| 2017/0224779 A1 | 8/2017 | Gong et al. | |

FOREIGN PATENT DOCUMENTS

WO  WO-2016112305 A1 * 7/2016 ............. A61K 45/06

OTHER PUBLICATIONS

Slusarz, Magdalena J; "Vasopressin V1a and V1b receptor modulators: a patent review (2012-2014)" Expert Opinion on Therapeutic Patents, 25, 711-722, 2015 (Year: 2015).*

(Continued)

*Primary Examiner* — David W Berke-Schlessel
(74) *Attorney, Agent, or Firm* — Timothy H. Van Dyke; Wolter Van Dyke Davis, PLLC

(57) ABSTRACT

Disclosed herein are methods and compositions for treating nonalcoholic fatty liver disease. Specifically exemplified herein is administration of compositions comprising a V1b inhibitor or V1a agonist or V1a stabilizer.

3 Claims, 7 Drawing Sheets

Fructose Induced Fatty Liver is Dependent on Vasopressin 1B Receptor

(56) References Cited

OTHER PUBLICATIONS

Donnellan, Fergal; et al; "Ischaemic complications of Glypressin in liver disease:a case series" British Journal of Clinical Pharmacology, 64, 550-552, 2007 (Year: 2007).*

Asferg CL, et al, "Copeptin, a surrogate marker for arginine vasopressin secretion, is associated with higher glucose and insulin concentrations but not higher blood pressure in obese men", Diabet Med 2014;31:728-32.

Aoyagi T, Birumachi J, Hiroyama M, et al. Alteration of glucose homeostasis in V1a vasopressin receptor-deficient mice. Endocrinology 2007;148:2075-84.

Andres M, Trueba M, Guillon G. Pharmacological characterization of F-180: a selective human V(1a) vasopressin receptor agonist of high affinity. Br J Pharmacol 2002;135:1828-36.

Enhorning S, Wang TJ, Nilsson PM, et al. Plasma copeptin and the risk of diabetes mellitus. Circulation 2010;121:2102-8.

Enhorning S, Bankir L, Bouby N, et al. Copeptin, a marker of vasopressin, in abdominal obesity, diabetes and microalbuminuria: the prospective Malmo Diet and Cancer Study cardiovascular cohort. Int J Obes (Lond) 2013;37:598-603.

Enhorning S, Struck J, Wirfalt E, Hedblad B, Morgenthaler NG, Melander O. Plasma copeptin, a unifying factor behind the metabolic syndrome. J Clin Endocrinol Metab 2011;96:E1065-72.

Fujiwara Y, Hiroyama M, Sanbe A, et al. Insulin hypersensitivity in mice lacking the V1b vasopressin receptor. The Journal of physiology 2007;584:235-44.

Fujiwara Y, Hiroyama M, Sanbe A, Yamauchi J, Tsujimoto G, Tanoue A. Mutual regulation of vasopressin- and oxytocin-induced glucagon secretion in V1b vasopressin receptor knockout mice. J Endocrinol 2007;192:361-9.

He X, Su F, Taccone FS, et al. A Selective V(1A) Receptor Agonist, Selepressin, Is Superior to Arginine Vasopressin and to Norepinephrine in Ovine Septic Shock. Crit Care Med 2016;44:23-31.

Hems DA, Whitton PD. Stimulation by vasopressin of glycogen breakdown and gluconeogenesis in the perfused rat liver. Biochem J 1973;136:705-9.

Itoh S, Yamada S, Mori T, et al. Attenuated stress-induced catecholamine release in mice lacking the vasopressin V1b receptor Am J Physiol Endocrinol Metab 2006;291:E147-51.

Koshimizu TA, Nakamura K, Egashira N, Hiroyama M, Nonoguchi H, Tanoue A. Vasopressin V1a and V1b receptors: from molecules to physiological systems. Physiol Rev 2012;92:1813-64.

Li JH, Jain S, McMillin SM, et al. A novel experimental strategy to assess the metabolic effects of selective activation of a G(q)-coupled receptor in hepatocytes in vivo. Endocrinology 2013;154:3539-51.

Maybauer MO, Maybauer DM, Enkhbaatar P, et al. The selective vasopressin type 1a receptor agonist selepressin (FE 202158) blocks vascular leak in ovine severe sepsis*. Crit Care Med 2014;42:e525-e33.

Rofe AM, Williamson DH. Metabolic effects of vasopressin infusion in the starved rat. Reversal of ketonaemia. Biochem J 1983;212:231-9.

Rofe AM, Williamson DH. Mechanism for the 'anti-lipolytic' action of vasopressin in the starved rat. Biochem J 1983;212:899-902.

Ryan ML, Falk DE, Fertig JB, et al. A Phase 2, Double-Blind, Placebo-Controlled Randomized Trial Assessing the Efficacy of ABT-436, a Novel V1b Receptor Antagonist, for Alcohol Dependence. Neuropsychopharmacology 2017;42:1012-23.

Saleem U, Khaleghi M, Morgenthaler NG, et al. Plasma carboxyterminal provasopressin (copeptin): a novel marker of insulin resistance and metabolic syndrome. J Clin Endocrinol Metab 2009;94:2558-64.

Serradeil-Le Gal C, Wagnon J, Valette G, et al. Nonpeptide vasopressin receptor antagonists: development of selective and orally active V1a, V2 and V1b receptor ligands. Prog Brain Res 2002;139:197-210.

Serradeil-Le Gal C, Wagnon J, Simiand J, et al. Characterization of (2S,4R)-1-[5-chloro-1[(2,4-dimethoxyphenyl) sulfonyl]-3-(2-methoxyphenyl)-2-oxo- 2,3-dihydro-1H-indol-3-yl]-4-hydroxy-N,N-dimethyl-2-pyrrolidine carboxamide (SSR149415), a selective and orally active vasopressin V1b receptor antagonist. J Pharmacol Exp Ther 2002;300:1122-30.

Sugimoto T, Saito M, Mochizuki S, Watanabe Y, Hashimoto S, Kawashima H. Molecular cloning and functional expression of a cDNA encoding the human V1b vasopressin receptor. J Biol Chem 1994;269:27088-92.

Taveau C, Chollet C, Waeckel L, et al. Vasopressin and hydration play a major role in the development of glucose intolerance and hepatic steatosis in obese rats. Diabetologia 2015;58:1081-90.

Tenderenda-Banasiuk E, Wasilewska A, Filonowicz R, Jakubowska U, Waszkiewicz-Stojda M. Serum copeptin levels in adolescents with primary hypertension. Pediatr Nephrol 2014;29:423-9.

Rene P, & De Keyzer Y, "The vasopressin receptor of corticotroph pituitary cells", Progress in Brain Research, vol. 139, pp. 345-357 (2002).

Wolf JP, Nguyen NU, Dumoulin G, Berthelay S. Influence of hypertonic monosaccharide infusions on the release of plasma arginine vasopressin in normal humans. Horm Metab Res 1992;24:379-83.

Spruce BA, McCulloch AJ, Burd J, et al. The effect of vasopressin infusion on glucose metabolism in man. Clin Endocrinol (Oxf) 1985;22:463-8.

Baertschi AJ, Friedli M. A novel type of vasopressin receptor on anterior pituitary corticotrophs? Endocrinology 1985;116:499-502.

Wisniewski K, Galyean R, Taki H, et al. Synthesis and in vitro pharmacological profile of potent and selective peptidic V1a receptor agonists. Adv Exp Med Biol 2009;611:507-8.

* cited by examiner

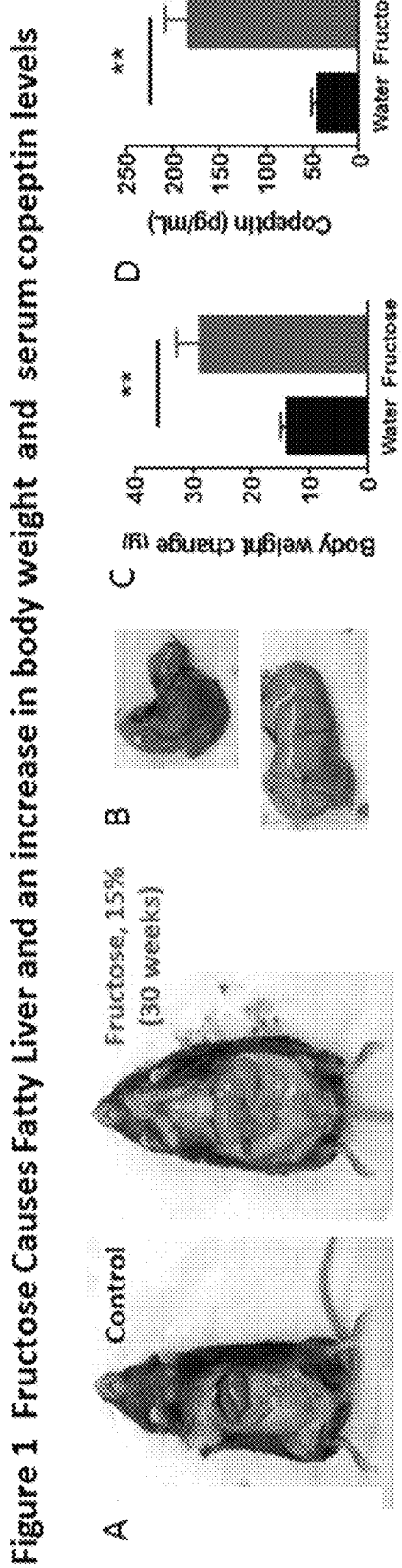

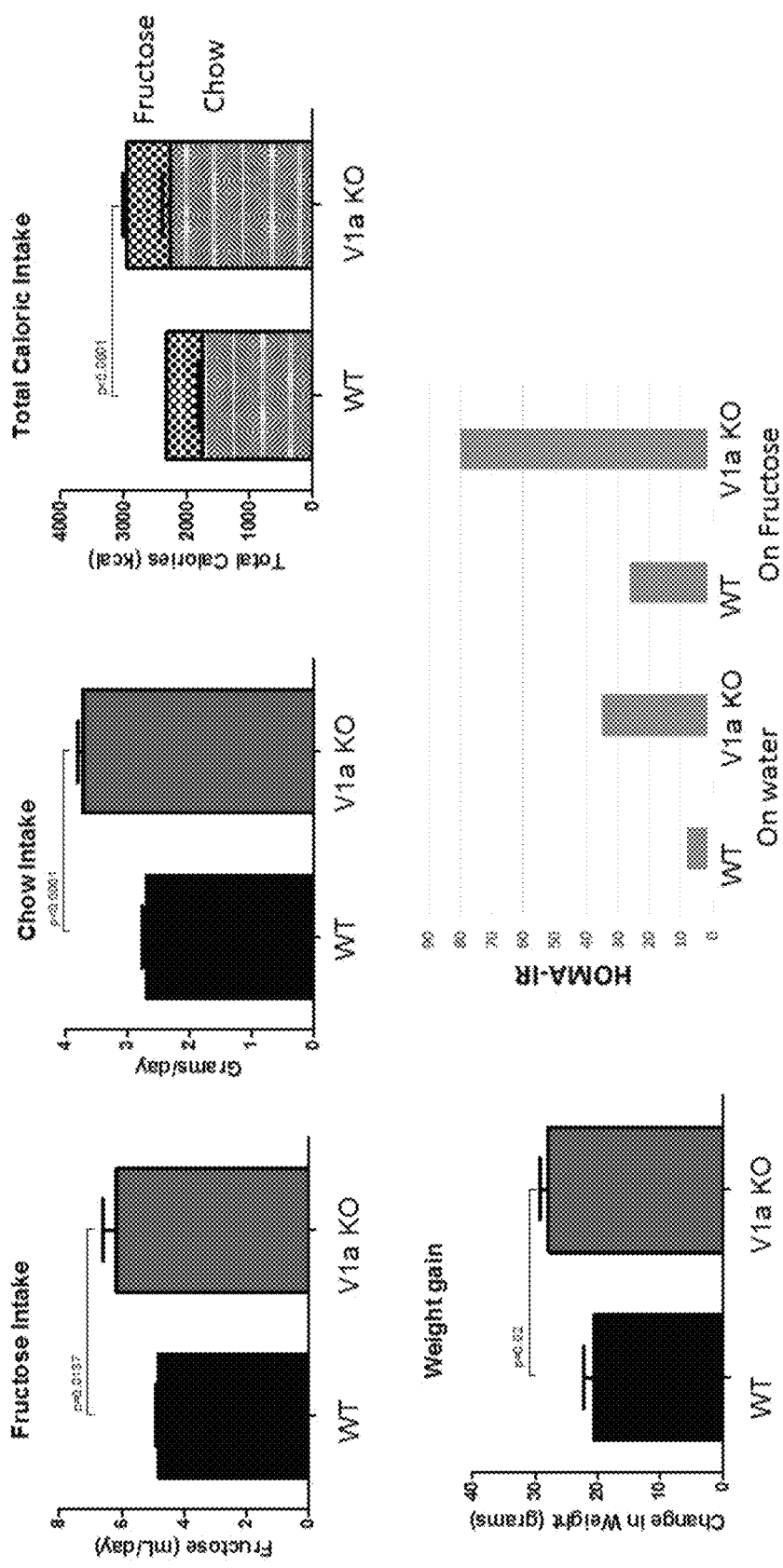

Figure 3 Wild type Mice and Vasopressin 1a receptor Knockout mice develop fatty liver with fructose
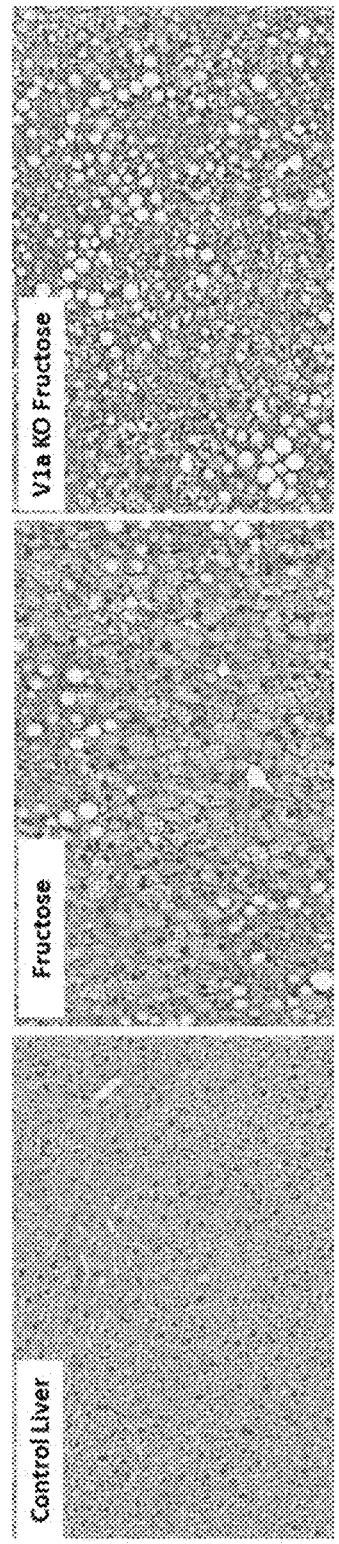
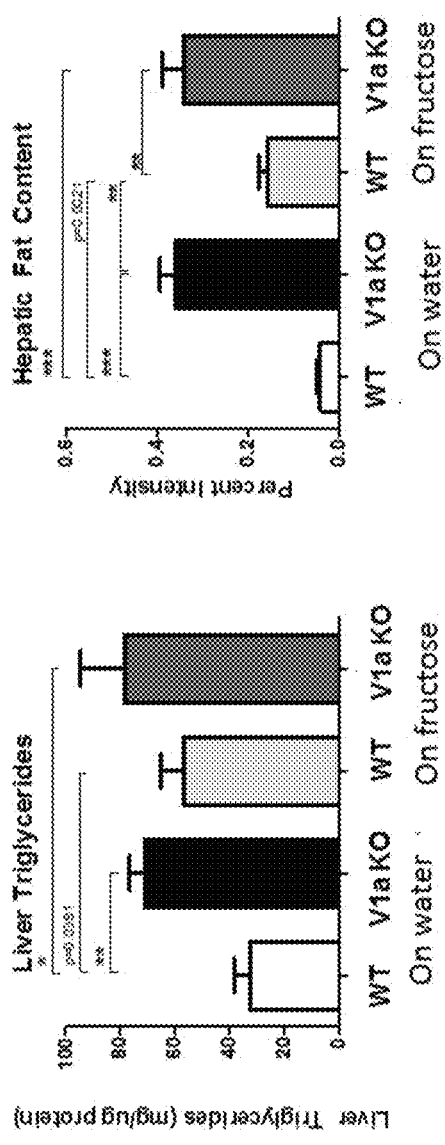
Figure 3 Representative H&E Stains from wild type (WT) and V1a receptor knockout (V1aKO) mice.

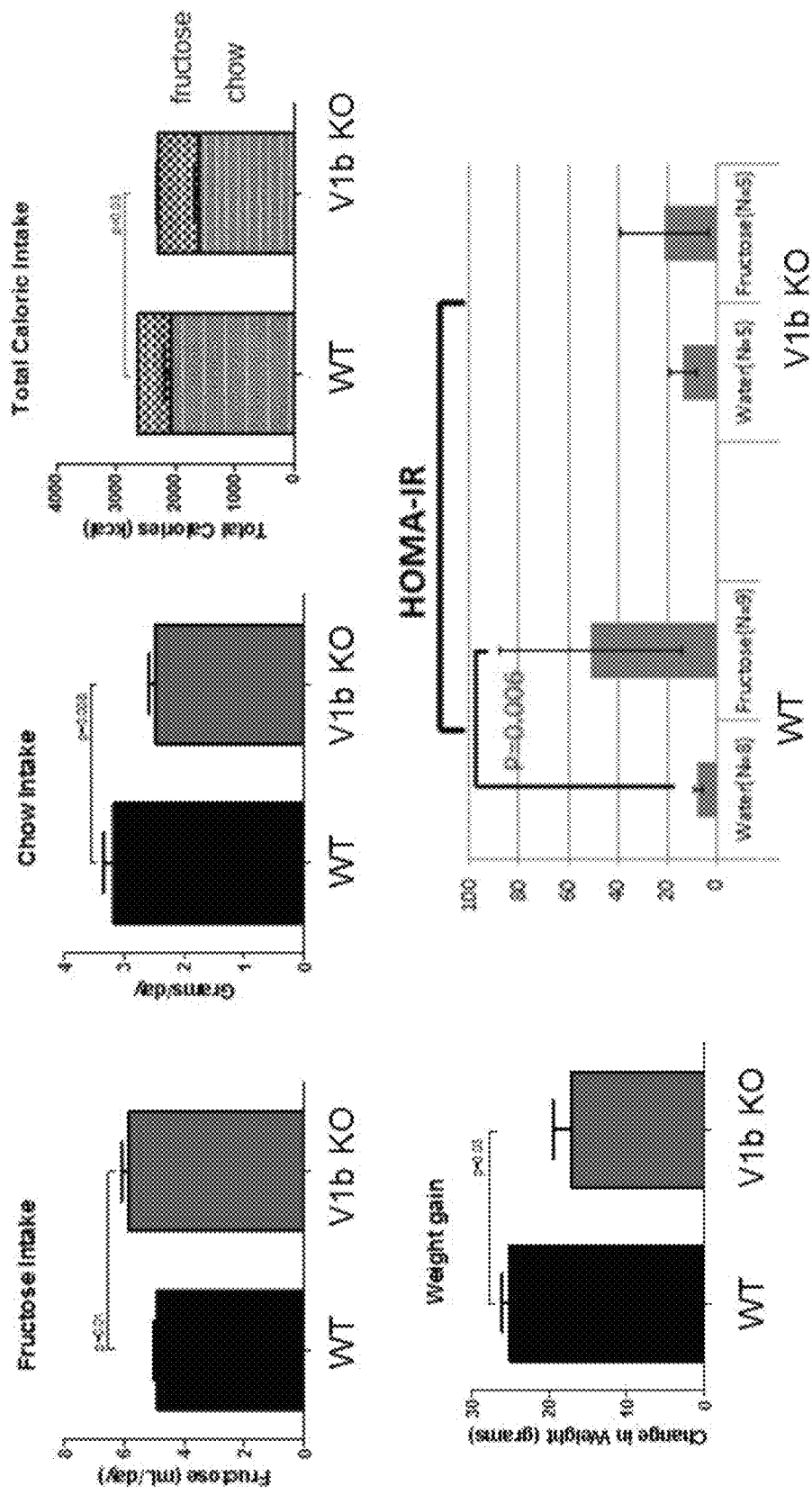

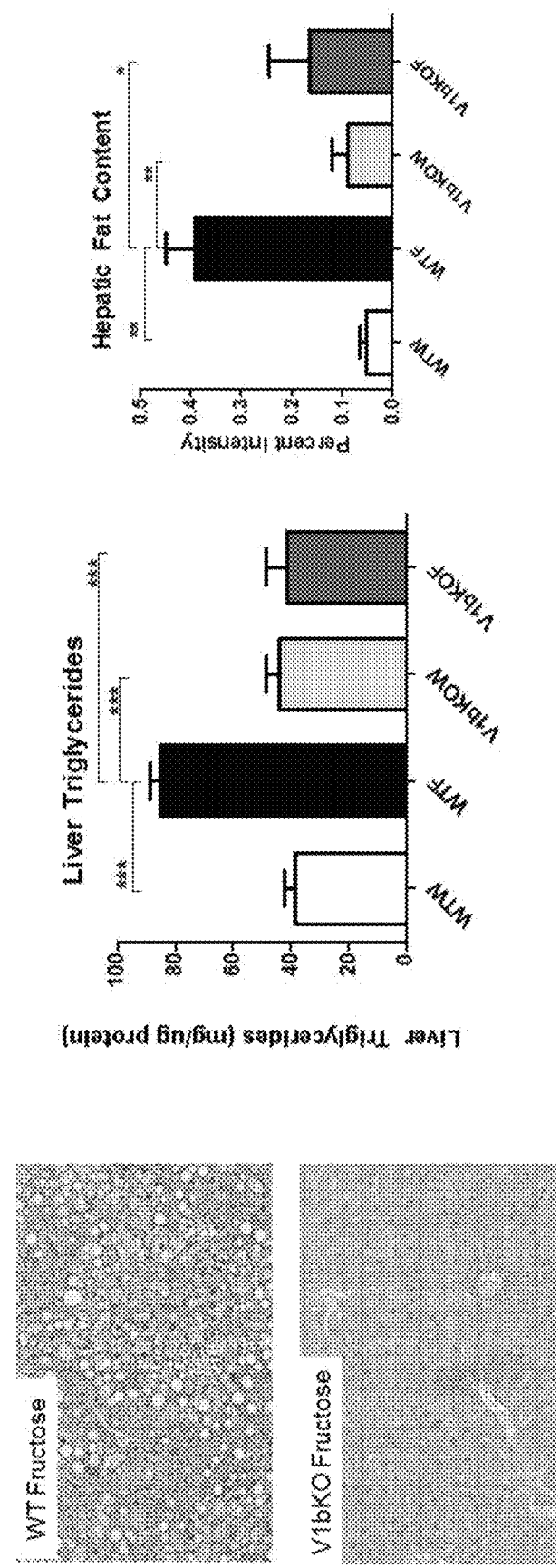

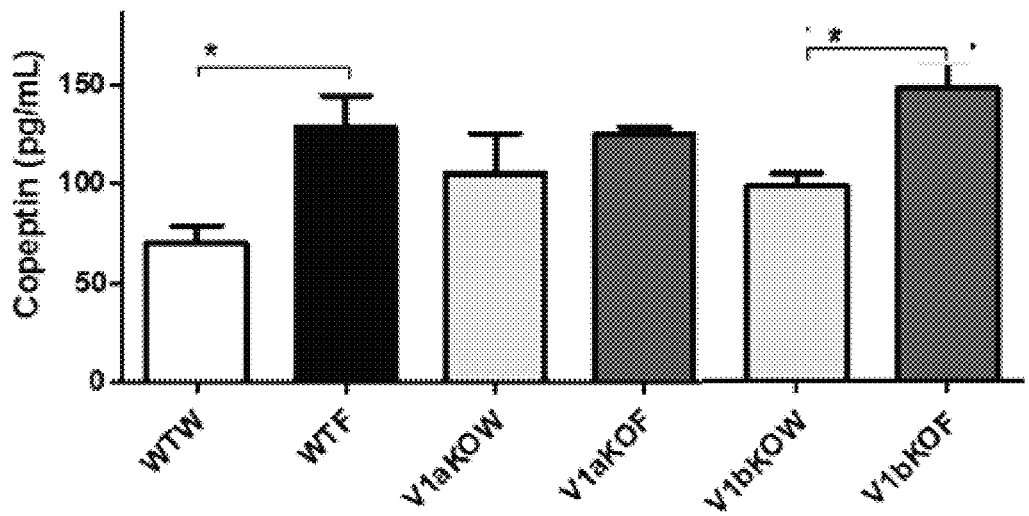
Figure 6 Serum Copeptin (Vasopressin biomarker) are high in V1aKO and V1bKO mice given fructose.
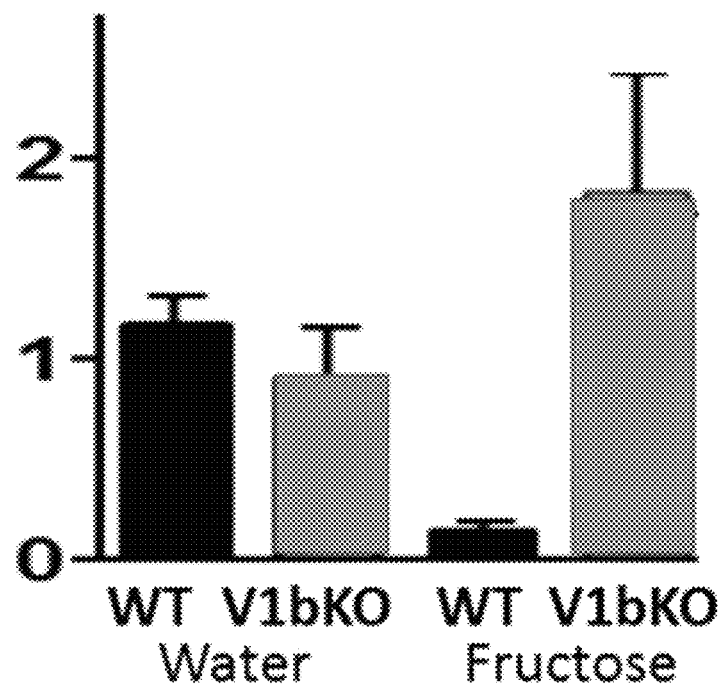
Figure 7. Hepatic V1a mRNA Expression (arbitrary units)

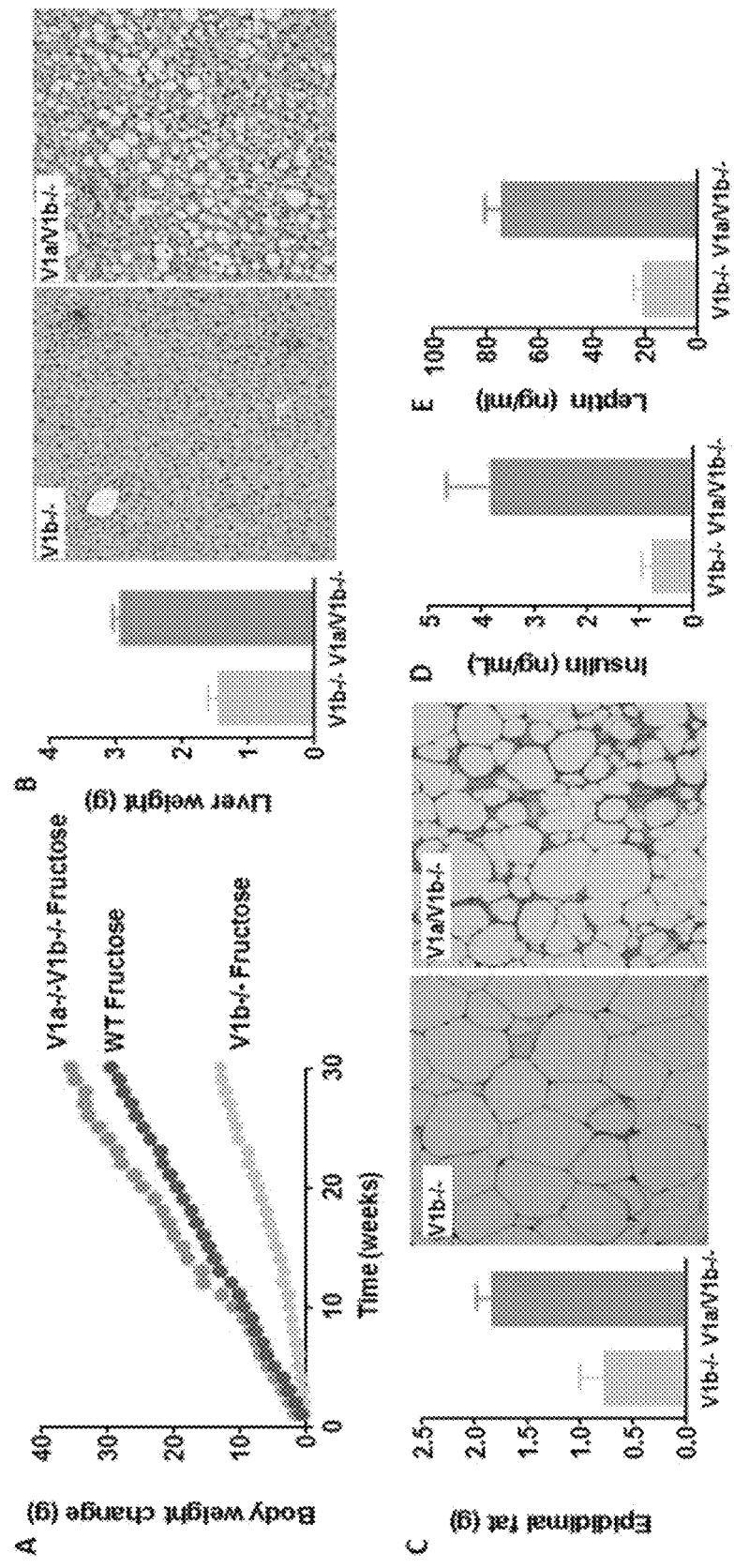
Figure 8. Effect of fructose on Double V1a and V1b Knockout Mice

SELECTIVE INHIBITION OF V1B FOR TREATING FATTY LIVER

GOVERNMENT SUPPORT

This invention was made with government support under grant number DK108408 awarded by national Institutes of Health. The government has certain rights in the invention.

BACKGROUND

Fatty liver, or hepatic steatosis, is a term that describes the buildup of fat in the liver. Fatty liver is a common condition, affecting around 10 to 20 percent of Americans without cirrhosis or inflammation. Most cases of fatty liver are detected in people between ages 40 and 60, according to the American Liver Foundation. Fatty liver can become harmful to the liver if its underlying cause isn't recognized and treated. The liver commonly repairs itself by rebuilding new liver cells when the old ones are damaged. When there's repeated damage to the liver, permanent scarring takes place. This condition is called cirrhosis.

Vasopressin is classically viewed as an antidiuretic hormone that responds to dehydration by stimulating water absorption by the kidney and concentrating the urine. However, subjects with metabolic syndrome frequently have elevated vasopressin levels as determined by measuring serum copeptin, which is a stable biomarker for serum vasopressin.[1-4] Serum copeptin not only is elevated in individuals with metabolic syndrome, but also predicts the development of obesity[5] or diabetes[5-6]. This has led to the concept that vasopressin may have a role in obesity and metabolic syndrome.

BRIEF DESCRIPTION OF THE DRAWINGS

FIG. 1: Fructose Causes Fatty Liver and an increase in body weight and serum copeptin levels FIG. 2: Vasopressin 1a receptor knockout mice eat more fructose and more calories and gain weight and show worse insulin resistance (HOMA-IR) than wild type mice on fructose.

FIG. 3: Wild type mice and vasopressin 1a receptor knockout mice develop fatty liver with fructose FIG. 4: Fructose Induced obesity is dependent on vasopressin 1b receptor.

FIG. 5: Fructose induced Fatty Liver is dependent on vasopressin 1b receptor.

FIG. 6: Serum copeptin (vasopressin biomarker) are high in V1aKO and B1bKO mice given fructose.

FIG. 7: Hepatic V1a mRNA Expression (arbitrary units)

FIG. 8: Effect of fructose on double V1a and V1b knockout mice.

DETAILED DESCRIPTION

Provided herein are novel methods of treating fatty liver disease that involve either inhibiting V1b or increasing/stabilizing activity of V1a, or both.

Overview

Role of Vasopressin in Metabolic Syndrome

Hyperglycemia. Vasopressin can induce a rise in serum glucose both in humans[7] and rodents[8-11].

Elevated blood pressure. Vasopressin is well known to cause vasoconstriction and a rise in blood pressure, and this is commonly used in intensive care units as a means to raise blood pressure.

Obesity/Fat. Vasopressin blocks fat oxidation,[8-9] and enhances fat accumulation by blocking lipolysis in fasting animals.[9,12,13]

Fatty Liver. Obese Zucker rats that are water-loaded reduced vasopressin levels and results in reduced fatty liver, suggesting a role for vasopressin in fatty liver.[14]

Role of Specific Receptors.

Vasopressin acts by binding specific vasopressin receptors. Vasopressin 2 receptors (V2 receptors) are highly expressed in the kidney and have a role in water reabsorption and urinary concentration. Blocking V2 receptors with the vaptans has become a major way to treat hyponatremic conditions due to high vasopressin levels.

Vasopressin can also bind vasopressin 1a receptors (V1a) (present in vascular smooth muscle and liver) and vasopressin 1b receptors (V1b) in the adrenal and pancreatic islets. V1a and V1b have both been proposed to have a role in metabolic syndrome.

V1a receptor (referred to herein as V1a). Vasopressin causes constriction of vascular smooth muscle cells and acute elevations of blood pressure via the V1a receptor.[12] Blocking V1a receptors with a specific inhibitor also improves insulin resistance in obese Zucker rats, suggesting that therapies aimed at blocking V1a may be useful. However, a lack of V1a also predisposes to insulin resistance and fat accumulation.[15]

V1b receptor (referred to herein as V1b). Vasopressin stimulates ACTH release from the pituitary via the V1b receptor[16,17] and catecholamine release from the adrenal medulla[18]

Definitions

Unless otherwise defined, all technical and scientific terms used herein are intended to have the same meaning as commonly understood in the art to which this invention pertains and at the time of its filing. Although various methods and materials similar or equivalent to those described herein can be used in the practice or testing of the present invention, suitable methods and materials are described below. However, the skilled should understand that the methods and materials used and described are examples and may not be the only ones suitable for use in the invention. Moreover, it should also be understood that as measurements are subject to inherent variability, any temperature, weight, volume, time interval, pH, salinity, molarity or molality, range, concentration and any other measurements, quantities or numerical expressions given herein are intended to be approximate and not exact or critical figures unless expressly stated to the contrary.

The term "enumerated agent" refers to an agent that inhibits activity or expression of V1b or that stabilizes or increases activity or expression of V1a.

The term "co-administration" "co-administer(ed)" or "co-administering" as used herein refers to the administration of an enumerated agent before, concurrently, or after the administration of another enumerated agent such that the biological effects of either agents overlap. The combination of agents as taught herein can act synergistically to treat or prevent the various diseases, disorders or conditions described herein. Using this approach, one may be able to achieve therapeutic efficacy with lower dosages of each agent, thus reducing the potential for adverse side effects.

The term "subject in need" refers to a subject that has one or more symptoms or markers of fatty liver disease, behavior profile, or corollary medical conditions, or who has been diagnosed with fatty liver disease.

The term "fatty liver disease" as used herein refers to non-alcoholic fatty liver disease (NAFLD) and alcohol related liver disease (ARLD).

The term "Nonalcoholic fatty liver disease" or "NAFLD" refers to a fatty liver disease characterized by the presence of fat (lipids) in the liver and no substantial inflammation or liver damage. NAFLD can progress into nonalcoholic steatohepatitis and then into irreversible, advanced liver scarring or cirrhosis. NAFLD includes a spectrum of histological forms including hepatic steatosis, and non-alcoholic steatohepatitis (NASH), which is characterized by liver inflammation, steatosis, necrosis and fibrosis due to the disruption of liver cells. NASH resembles alcoholic liver disease, but occurs in people who drink little or no alcohol. The major feature in NASH is fat in the liver, along with inflammation and damage. NASH can lead to cirrhosis, in which the liver is permanently damaged and scarred and is no longer able to function properly. A differential diagnosis of NASH versus NAFLD may be determined by liver biopsy. NAFLD may include nonalcoholic steatohepatitis (NASH) or nonalcoholic cirrhosis.

Individuals with NAFLD may be asymptomatic but clinical lab tests can show elevated liver enzyme levels. Individuals may exhibit symptoms of NAFLD, such as abdominal discomfort (e.g., discomfort in the right upper abdominal quadrant), acanthosis nigricans, bowel dismotility, coma, constipation, disseminated intravascular coagulopathy, epigastric pain, fatigue, malaise, hepatomegaly (generally with a smooth, firm surface upon palpation), hypoglycemia, jaundice, lipomatosis, lipoatrophy, lipodystrophy, nausea, neurological defects, Palmer erythema, panniculitis, periumbilical pain, small bowel bacterial overgrowth, spider angiomata, splenomegaly, subacute liver failure, and vomiting. Clinical evaluation to rule out alcohol related fatty liver disease may include determining if the individual consumes excess alcohol (e.g., >60 g/day for men and >20 g/day for women within the past 5 years. The presence or level of anti-hepatitis C antibody and serum ceruloplasmin levels can be used to look for other causes of liver disease besides NAFLD.

In an individual suspected of having NAFLD or NASH, baseline testing of serum may include measuring or determining levels of AST, ALT, total and direct bilirubin, and fasting serum glucose, as well as a lipid panel. For example, steatosis may be indicated by elevated serum levels (often moderately elevated, e.g., elevated approximately 2, 3, 4, 5, 6, 7, 9, 10, 11, or 12-fold above normal levels) of liver enzymes (such as, e.g., AST, ALT, GGT and alkaline phosphatase) when other causes (such as, e.g., acute hepatitis, autoimmune disease, chronic hepatitis, cirrhosis, fulminant hepatitis, hepatocellular carcinoma, metastatic carcinoma, right heart failure, and viral hepatitis) have been eliminated. For example, ALT values greater than 32, 24, or 56 units per liter of serum or at least 2, 3, 4, 5, 6, 7, 8, 9, 10, 11, 12, or more times normal values may be indicative of a disorder associated with hepatic lipid deposits, or by AST values greater than 40 units per liter of serum or at least 2, 3, 4, 5, 6, 7, 8, 9, 10, 11, 12, or more times normal values. Mild to moderate elevation of serum aminotransferase levels is most commonly found (mean range, 100-200 IU/L). The ratio of AST/ALT is often less than one in NAFLD, but may be greater than one in patients with alcoholic liver disease or advanced liver disease or if the patient advances to fibrosis. GGT levels may also be significantly elevated, e.g., at least 2, 3, 4, 5, 6, 7, 8, 9, 10, 11, 12, or more times normal values as defined by a normal, healthy individual. Liver enzyme levels can be normal in a large percentage of patients with NAFLD, thus normal AST or ALT levels do not exclude the presence of advanced disease. Serum alkaline phosphatase and GGT levels may be mildly abnormal. Given that more than 80% of patients with NAFLD have some components of metabolic syndrome, serum levels of fasting cholesterol and triglycerides, as well as fasting glucose and insulin, may be determined. Albumin, bilirubin, and platelet levels may be normal unless the disease has evolved to cirrhosis. Some patients with NAFLD have low titers of autoimmune antibodies (e.g., antinuclear and anti-smooth muscle antibody) and an elevation of ferritin (Carey et al., "Nonalcoholic Fatty Liver Disease" in *Current Clinical Medicine*, $2^{nd}$ edition, Elsevier, New York. In some embodiments, an AST/ALT ratio of greater than 1 can predict more advanced fatty liver disease.

Some have also reported that high serum uric acid levels are common in subjects with NAFLD, and that NAFLD may occur in subjects with normal or low BMI, especially when serum uric acid levels are high.

Radiologic methods such as, but not limited to, x-ray imaging, ultrasonography, computed tomography (CT), magnetic resonance imaging (MRI), and magnetic resonance spectroscopy can be used to detect NAFLD. With ultrasonography, increased echogenicity of the liver compared to the kidneys can indicate liver steatosis.

NASH can be diagnosed using histopathological methods on liver samples (e.g., biopsies) to assess macrovesicular steatosis, ballooning degeneration, hepatocyte necrosis, lobular inflammation, megamitochondria, infiltration of inflammatory cells, apoptosis, and fibrosis (see, e.g., Brunt and Tiniakos, *World J Gastroenterol*, 2010, 16(42):5286-8296). Hepatocytic ballooning is characterized by swelling and enlargement of the cells, and sometimes the appearance of cytoplasmic alterations containing Mallory-Denk bodies. Fibrosis can also develop over time, initially as pericellular/pervenular fibrosis and eventually to portal-central bridging fibrosis and cirrhosis.

Hematoxylin and eosin (H&E), Masson trichrome, Oil Red O and immunohistochemical staining and other standard histological methods known to those of ordinary skill in the art can be performed to analyze tissue and cellular features. A scoring system (e.g., a NAFLD activity score) that includes one or more histological features can be used to score and diagnose NAFLD, including NASH. In some embodiments, the NASH Clinical Research Network Scoring System developed by the Pathology Committee of the NASH Clinical Research Network (see, e.g., Kleiner et al., *Hepatology*, 2005, 41(6): 1313-1321) can be used predict whether an individual has NAFLD or NASH. The Practice Guidelines published by the American Gastroenterological Association, American Association for the Study of Liver Diseases, and American College of Gastroenterology (Chalasani et al., *Gastroenterology*, 2012, 142: 1592-1609) can be followed by a clinician to diagnose or monitor NAFLD, including non-alcoholic fatty liver, NASH and NASH associated cirrhosis.

The term "Alcohol-related liver disease" or "ARLD" refers to diseases of the liver that are wholly, or in part, caused by, or attributable to, excessive consumption of alcohol. There are four main types of ARLD, alcoholic fatty liver (AFL, a sub-type of fatty liver disease), alcoholic steatohepatitis (ASH), alcoholic-induced cirrhosis, and alcoholic hepatocellular cancer. As used herein, "excessive consumption of alcohol" generally refers to the consumption of more than about 15-30 g/day of ethanol. Virtually all persons who are chronic and heavy consumers of alcohol will develop AFL. Additionally, due to the high prevalence of complicating factors such as obesity, diabetes, and metabolic syndrome in the general population, many individuals who do not satisfy the criteria for chronic heavy consumers of alcohol are susceptible to developing AFL.

AFL can also be indicated by, and thus diagnosed due to, presentation of one or more symptoms or risk factors (e.g., obesity, diabetes, drinking behavior, etc.). Fatty liver disease can present symptoms such as fatigue, muscle weakness, abdominal discomfort, weight loss, and confusion. However, fatty liver disease usually does not present overt physical symptoms. Fatty liver disease can also be accompanied by, or precede, inflammation of the liver or hepatic fibrosis. Patients with fatty liver disease generally present elevated serum liver enzyme levels. Moreover, the relative levels of several liver enzymes are altered. AFL generally presents with a serum aspartate aminotransferase (AST) level that is greater than the level of alanine aminotransferase (ALT). This is distinguished from non-alcoholic fatty liver disease, in which ALT is higher than AST.

AFL can be diagnosed via ultrasound. Typically, the liver of a patient with AFL presents as "echogenic," meaning more dense than usual to the imaging sound waves. In addition, the liver is typically enlarged due to the swelling and presence of large amounts of fat.

A "therapeutically effective amount" refers to an amount of an enumerated agent, which, when administered or co-administered in a proper dosing regimen, is sufficient to reduce or ameliorate the severity, duration, or progression of the disorder being treated (e.g., fatty liver disease), prevent the advancement of the disorder being treated (e.g., fatty liver disease), cause the regression of the disorder being treated (e.g., fatty liver disease), or enhance or improve the prophylactic or therapeutic effects(s) of another therapy. The full therapeutic effect does not necessarily occur by administration of one dose and may occur only after administration of a series of doses. Thus, a therapeutically effective amount may be administered in one or more administrations per day for successive days.

The terms "treat", "treating" or "treatment of" as used herein refers to providing any type of medical management to a subject. Treating includes, but is not limited to, administering a composition comprising one or more enumerated agents to a subject using any known method. for purposes such as curing, reversing, alleviating, reducing the severity of, inhibiting the progression of, or reducing the likelihood of a disease, disorder, or condition or one or more symptoms or manifestations of a disease, disorder or condition.

Enumerated Agents

Examples of enumerated agents that can be used in accord with the teachings herein include those taught in the following references:

US Patent Publication No. 2017/0224779 (METHODS FOR TREATING CARDIOVASCULAR DYSFUNCTION AND IMPROVING FLUID HOMEOSTASIS WITH A PEPTIDE HORMONE).

US Patent Publication No. 2009/0181909 (Vasopressin-Binding L-Nucleic Acid, to Werner Purschke, owned by Noxxon Pharma AG, filed Nov. 29, 2005) claims the use of a vasopressin antagonist peptide.

U.S. Pat. No. 8,148,319 (Peptidic vasopressin receptor agonists, to Wisniewski et al, owned by Ferring BV, filed Aug. 3, 2008) discloses agonists of the human V1a receptor and methods of treating shock using the same.

U.S. Pat. No. 8,222,202 (Use of peptidic vasopressin receptor agonists, to Laporte and Riviere, owned by Ferring BV, filed Feb. 12, 2007) discloses agonists of the human V1a receptor and methods of treating hypertensive disorders and syndromes secondary to shock or immune reaction, including hypertension induced by end-stage renal disease, using the same.

U.S. Pat. No. 8,461,152 (Arylcyclohexylethers of dihydrotetraazabenzoazulenes, to Patrick Schnider, owned by Hoffman-La Roche, filed May 15, 2012) discloses antagonists of the human V1a receptor and methods of treating hypertension and chronic heart failure using the same.

US Patent Publication No. 2008/0275026 (Benzamide derivatives as oxytocin agonists and vasopressin antagonists, to Hudson et al, owned by Ferring BV, filed Jun. 20, 2008) claims the use of a vasopressin V1a agonists for the treatment of erectile dysfunction and primary dysmenorrhea using the same.

U.S. Pat. No. 8,431,567 (Substituted oxindole derivatives and their use as vasopressin and/or oxytocin receptor ligands, to Geneste et al., owned by Abbott, filed Aug. 24, 2007) discloses modulators of vasopressin receptors V1b and V1a and methods of using the same.

U.S. Pat. No. 8,546,401 (5,6-disubstituted oxindole-derivatives and use thereof for treating vasopressin-dependent diseases, to Braje et al., owned by Abbott, filed Dec. 5, 2008) discloses antagonists of V1b vasopressin receptors and methods of using the same.

U.S. Pat. No. 8,580,842 (Heteroaryl-substituted 1,3-dihydroindol-2-one derivatives and medicaments containing them, to Wilfried et al., owned by Abbott, filed Jul. 20, 2010) discloses antagonists of V1b vasopressin receptors and methods of using the same.

U.S. Pat. No. 8,703,774 (Carbamate-substituted oxindole derivatives and use thereof for the treatment of vasopressin-dependent diseases, to Netz et al., owned by Abbvie, filed Dec. 5, 2008) discloses antagonists of V1b vasopressin receptors and methods of using the same.

U.S. Pat. No. 8,703,775 (Amidomethyl-substituted oxindole derivatives and the use thereof for the treatment of vasopressin-dependent illnesses, to Oost et al., owned by Abbvie, filed Dec. 5, 2008) discloses antagonists of V1b vasopressin receptors and methods of using the same.

Other enumerated agents include:

TS-121 (Taisho pharmaceutical)-selective V1b receptor antagonist

F-180[24] a vasopressin analogue, specifically binds human V1a receptors.

Selepressin, a new V1 receptor agonist[25,26] (also known as (FE 202158) developed by Ferring Research institute in 2009[27]

Nelivaptan is a specific orally available V1b receptor antagonist (Ki 1.5 nM) with little effects on V1a-Ki 100 fold greater than for V1b- and V2 receptors (Axon Medchem). same as 2S,4R)-1-[5-chloro-1-[(2,4-dimethoxyphenyl) sulfonyl]-3-(2-methoxy-phenyl)-2-oxo-2,3-dihydro-1H-indol-3-yl]-4-hydroxy-N,N-dimethyl-2-pyrrolidine carboxamide (SSR149415)[21-22] (Sanofi)

ABT-436 and ABT-558[23] orally active V1b receptor antagonists.

Other enumerated agents include inhibitory oligonucleotides such as siRNA, shRNA, antisense molecule, miRNA or ribozyme, or antibodies or aptamers, peptides that inhibit V1b preferentially over V1a, or which stabilize or increase activity of V1a. See for example ThermoFisher (Cat. No. AM16708).

The above cited references to enumerated agents are incorporated herein by reference.

Pharmaceutical Compositions and Administration

Enumerated agents useful in therapeutic methods described herein may be provided in a formulation or composition acceptable for administration to a subject. Typically, agent(s) are provided with a pharmaceutically acceptable carrier. "Pharmaceutically acceptable carrier" is intended to include any and all solvents, binders, diluents, disintegrants, lubricants, dispersion media, coatings, antibacterial and antifungal agents, isotonic and absorption delaying agents, and the like, compatible with pharmaceutical administration. The use of such media and agents for pharmaceutically active substances is well known in the art. As long as any conventional media or agent is compatible with the active agent, such media can be used in the compositions of the invention and supplementary active agents or therapeutic agents can also be incorporated into the compositions. A pharmaceutical composition of the invention is formulated to be compatible with its intended route of administration.

Solutions or suspensions can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylene diamine tetra acetic acid; buffers such as acetates, citrates or phosphates and agents for the adjustment of tonicity such as sodium chloride or dextrose. pH can be adjusted with acids or bases, such as hydrochloric acid or sodium hydroxide.

Pharmaceutical compositions suitable for injectable use include sterile aqueous solutions (where the enumerated agents are water soluble) or dispersions and sterile powders for the extemporaneous preparation of sterile injectable solutions or dispersion. For intravenous administration, suitable carriers include physiological saline, bacteriostatic water, Cremophor EL® (BASF, Parsippany, N.J.) or phosphate buffered saline (PBS). In all cases, the composition must be sterile and should be fluid to the extent that easy syringability exists. It should be stable under the conditions of manufacture and storage and should be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Further details on techniques for formulation and administration can be found in the latest edition of REMINGTON'S PHARMACEUTICAL SCIENCES (Maack Publishing Co., Easton, Pa., which is incorporated herein by reference). After pharmaceutical compositions have been prepared, they can be placed in an appropriate container and labeled for treatment of an indicated condition. Such labeling would include amount, frequency, and method of administration.

Enumerated agents may be administered by one of multiple modes of administration. Modes of administering include, but are not limited to oral administration, parenteral administration such as intravenous, subcutaneous, intramuscular or intraperitoneal injections, rectal administration by way of suppositories, transdermal administration, intraocular administration or administration by any route or method that delivers a therapeutically effective amount of the drug or composition to the cells or tissue to which it is targeted. Alternatively, routine experimentation will determine other acceptable routes of administration. When it is desirable to deliver them systemically, may be formulated for parenteral administration by injection, e.g., by bolus injection or continuous infusion. Formulations for injection may be presented in unit dosage form, e.g., in ampoules or in multi-dose containers. Pharmaceutical parenteral formulations include aqueous solutions of the ingredients. Aqueous injection suspensions may contain substances which increase the viscosity of the suspension, such as sodium carboxymethyl cellulose, sorbitol, or dextran. Alternatively, suspensions of ingredients may be prepared as oil-based suspensions. Suitable lipophilic solvents or vehicles include fatty oils such as sesame oil, or synthetic fatty acid esters, such as ethyl oleate or triglycerides.

EXAMPLES

Fructose, Vasopressin and Fatty Liver.

Fructose is a simple sugar that is a component of sucrose as well as high fructose corn syrup (HFCS). Fructose is now recognized as a major cause of fatty liver in animals and humans. Of interest, previous studies have shown that fructose, but not glucose, directly stimulates vasopressin release.[19] This observation was ignored for nearly 25 years. However, recently it has also been found that the administration of fructose orally to mice induces a rise in vasopressin (copeptin) in the blood in association with weight gain and the development of an enlarged, fatty liver (FIG. 1).

FIG. 1 shows the effect of fructose provided in the drinking water (15% for 30 weeks) on body size (Figure A) as well as on liver size. While normal liver is light red and small (Figure B, upper), fatty liver from fructose fed mice is pale, white or creamy, and enlarged (Fig B, lower panel). Body weight is increased after 30 weeks (Figure C) and fasting serum copeptin (a biomarker of vasopressin) is elevated in fructose-fed mice.

These studies suggest vasopressin may have a role in fatty liver, but the specific receptor driving this response has not been known. Taveau et al had suggested that stimulation of the V1a receptors may be important, as V1a is the primary vasopressin receptor expressed in the liver, and because blocking V1a can block other aspects of the metabolic syndrome such as insulin resistance.[14]

Novel and Contrasting Roles for V1a and V1b in Driving Fatty Liver.

V1a receptor knockout are not protected from fructose. One of the most important and unanticipated discoveries provided herein was that the vasopressin 1a and 1b receptors have opposing effects on the development of fatty liver in response to fructose. It was found that V1a receptor knockout, which were predicted to prevent fructose-induced metabolic syndrome based on actions of vasopressin[12,14], actually exacerbated metabolic syndrome and fatty liver (FIGS. 2 and 3).

FIG. 2 shows the effects of dietary fructose (15% in the drinking water) on V1a receptor knockout mice. V1a receptor knockout mice (V1aKO) actually prefer fructose to wild type (WT) mice, and ingest more fructose, while still eating more chow. The consequence is greater weight gain after 30 weeks. This is associated with worsening insulin resistance (noted by HOMA-IR) in V1aKO mice than WT mice, both when on a normal diet or when on a high fructose diet.

FIG. 3 shows the effect of fructose on the development of fatty liver in V1a knockout mice (V1aKO) compared to wild type (WT) mice. Compared to control liver, fructose fed WT mice showed fatty liver as noted by the vacuoles of fat. V1aKO mice also developed fatty liver, even when on normal chow and water. Thus V1aKO mice were not protected from fatty liver, and tended to have higher liver fat content regardless of fructose intake.

V1b receptor knockout mice are protected from metabolic syndrome and fatty liver. While V1a receptor knockout mice tended to show worsening metabolic features and fatty liver in response to fructose compared to wild type mice, V1b receptor knockout mice were completely protected from the effects of fructose, including the development of fatty liver (FIG. 4 and FIG. 5).

FIG. 4 shows the effect of fructose provided in the drinking water (15%) to wild type (WT) or vasopressin 1b receptor knockout mice (V1bKO) for 30 weeks. V1b knockout mice like fructose, and actually ingested more fructose than WT mice. However, unlike the V1a knockout mice, who also ate more chow, the V1b KO compensated by eating less chow with significantly less total energy (calorie) intake. This was associated with less weight gain than WT mice on fructose. Similarly, while WT mice fed fructose developed insulin resistance (high HOMA-IR indices) compared to WT mice drinking water, V1bKO mice were largely protected from developing insulin resistance in response to fructose.

FIG. 5 shows the effect of fructose provided in the drinking water (15%) to wild type (WT) or vasopressin 1b receptor knockout mice (V1bKO) for 30 weeks. Fructose given to WT mice resulted in fatty liver, as noted in hematoxylin stained sections by the fatty vacuoles, but this was not observed in V1b receptor knockout mice who also had less triglyceride accumulation and an overall lower hepatic fat content (oil red O stain).

Interestingly, fructose increased vasopressin levels in the circulation in both the V1aKO and V1bKO mouse given fructose, showing that vasopressin levels were high in both groups despite the marked contrasting effects of fructose in V1a and V1b knockout mice (FIG. 6).

FIG. 6 shows serum copeptin levels at 30 weeks in wild type mice given water (WTW) or fructose (WTF) as well as V1aKO and V1bKO mice on water (V1aKOW and V1abKOW) or fructose (V1aKOF and V1bKOF, respectively). As can be seen, both fructose fed wild type mice and V1bKO mice showed an increase in serum copeptin levels with fructose, while V1a KO mice tended to have higher serum copeptin levels irrespective of whether they ingested fructose or not.

These studies show that knocking down V1b receptors are useful for the treatment of metabolic syndrome and fatty liver, while stimulating V1a receptors might be protective. This dichotomy of effects on vasopressin receptors has not been previously noted in the literature.

Double Knockout V1a and V1b Knockout Mice are not Protected from Fructose Induced Fatty Liver and Metabolic Syndrome.

As mentioned, the V1a receptor is on the liver cells and it was found that the V1a receptor was significantly lower in mice administered fructose, but preserved in mice lacking V1b (FIG. 7).

This raised the possibility that the protection of V1b is primarily to preserve expression of V1a in the liver. To investigate this possibility, mice were generated that lack both the V1a and V1b receptor, but still express the V2 vasopressin receptor. When fructose was administered to the V1a and V1b receptor double knockout, there was no protection against metabolic syndrome or fatty liver to fructose (FIG. 8).

This suggests that simple blockade of vasopressin will not be sufficient to protect animals from metabolic syndrome (unexpected finding), and that protection from vasopressin will have to either consist of stimulation and/or preservation of V1a receptor, and or blockade of vasopressin 1b receptor. It is believed that the concept that one has to block one receptor, but stimulate the other has not been disclosed previously.

FIG. 8 shows the effects of fructose in the V1a and V1b double knockout mouse treated with fructose in the drinking water (15%) for 30 weeks. Figure A shows weekly body weight gain on wild type (WT), V1b receptor knockout (V1b−/−) and double receptor knockout (V1a/V1b−/−) mice fed fructose for 30 weeks. Figure B shows liver weight at sacrifice and representative hematoxylin and eosin stained tissues from fructose fed V1b−/− and V1a/V1b−/− mice. Unlike V1b−/− mice, V1a/V1b−/− mice demonstrate severe micro- and macrosteatotic areas and inflammation. Figure C shows epididymal fat weight at sacrifice and representative histology from fructose fed V1b−/− and V1a/V1b−/− mice. Unlike V1b−/− mice, V1a/V1b−/− mice demonstrate focal inflammation denoted as "crown structures". Figure D shows fasting insulin and serum leptin in these same animals.

Novel Mechanisms for Treating Fatty Liver.

V1b Receptor Antagonists. Without being bound to any particular theory, these studies suggest a specific blocker for vasopressin 1b should block metabolic syndrome and fatty liver, whereas protection might not be observed with an agent that blocks both V1a and V1b receptors. There has been claims that V1b inhibition might aid insulin resistance[20], but not for fatty liver (nonalcoholic fatty liver disease). The studies herein demonstrate that V1b blockade will protect against fatty liver.

As will be apparent to one of ordinary skill in the art from a reading of this disclosure, further embodiments of the present invention can be presented in forms other than those specifically disclosed above. The particular embodiments described above are, therefore, to be considered as illustrative and not restrictive. Those skilled in the art will recognize, or be able to ascertain, using no more than routine experimentation, numerous equivalents to the specific embodiments described herein. Such equivalents are considered to be within the scope of this invention. Although the invention has been described and illustrated in the foregoing illustrative embodiments, it is understood that the present disclosure has been made only by way of example, and that numerous changes in the details of implementation of the invention can be made without departing from the spirit and scope of the invention, which is limited only by the claims that follow. Features of the disclosed embodiments can be combined and rearranged in various ways within the scope and spirit of the invention. The scope of the invention is as set forth in the appended claims and equivalents thereof, rather than being limited to the examples contained in the foregoing description. The teachings of the cited references are incorporated herein in their entirety to the extent not inconsistent with the teachings herein.

REFERENCES—CORRELATING TO THOSE INDICATED ABOVE AS SUPERSCRIPTS

1. Asferg C L, Andersen U B, Linneberg A, Goetze J P, Jeppesen J L, Copeptin, a surrogate marker for arginine vasopressin secretion, is associated with higher glucose and insulin concentrations but not higher blood pressure in obese men. Diabet Med 2014; 31:728-32.
2. Saleem U, Khaleghi M, Morgenthaler N G, et al. Plasma carboxy-terminal provasopressin (copeptin): a novel marker of insulin resistance and metabolic syndrome. J Clin Endocrinol Metab 2009; 94:2558-64.
3. Enhorning S, Struck J, Wirfalt E, Hedblad B, Morgenthaler N G, Melander O. Plasma copeptin, a unifying factor behind the metabolic syndrome. J Clin Endocrinol Metab 2011; 96:E1065-72.
4. Tenderenda-Banasiuk E, Wasilewska A, Filonowicz R, Jakubowska U, Waszkiewicz-Stojda M. Serum copeptin levels in adolescents with primary hypertension. Pediatr Nephrol 2014; 29:423-9.
5. Enhorning S, Bankir L, Bouby N, et al. Copeptin, a marker of vasopressin, in abdominal obesity, diabetes and microalbuminuria: the prospective Malmo Diet and Cancer Study cardiovascular cohort. Int J Obes (Lond) 2013; 37:598-603.
6. Enhorning S, Wang T J, Nilsson P M, et al. Plasma copeptin and the risk of diabetes mellitus. Circulation 2010; 121:2102-8.
7. Spruce B A, McCulloch A J, Burd J, et al. The effect of vasopressin infusion on glucose metabolism in man. Clin Endocrinol (Oxf) 1985; 22:463-8.
8. Hems D A, Whitton P D. Stimulation by vasopressin of glycogen breakdown and gluconeogenesis in the perfused rat liver. Biochem J 1973; 136:705-9.
9. Rofe A M, Williamson D H. Metabolic effects of vasopressin infusion in the starved rat. Reversal of ketonaemia. Biochem J 1983; 212:231-9.
10. Fujiwara Y, Hiroyama M, Sanbe A, et al. Insulin hypersensitivity in mice lacking the V1b vasopressin receptor. The Journal of physiology 2007; 584:235-44.
11. Fujiwara Y, Hiroyama M, Sanbe A, Yamauchi J, Tsujimoto G, Tanoue A. Mutual regulation of vasopressin- and oxytocin-induced glucagon secretion in V1b vasopressin receptor knockout mice. J Endocrinol 2007; 192:361-9.
12. Koshimizu T A, Nakamura K, Egashira N, Hiroyama M, Nonoguchi H, Tanoue A. Vasopressin V1a and V1b receptors: from molecules to physiological systems. Physiol Rev 2012; 92:1813-64.
13. Rofe A M, Williamson D H. Mechanism for the 'antilipolytic' action of vasopressin in the starved rat. Biochem J 1983; 212:899-902.
14. Taveau C, Chollet C, Waeckel L, et al. Vasopressin and hydration play a major role in the development of glucose intolerance and hepatic steatosis in obese rats. Diabetologia 2015; 58:1081-90.
15. Aoyagi T, Birumachi J, Hiroyama M, et al. Alteration of glucose homeostasis in V1a vasopressin receptor-deficient mice. Endocrinology 2007; 148:2075-84.
16. Sugimoto T, Saito M, Mochizuki S, Watanabe Y, Hashimoto S, Kawashima H. Molecular cloning and functional expression of a cDNA encoding the human V1b vasopressin receptor. J Biol Chem 1994; 269:27088-92.
17. Baertschi A J, Friedli M. A novel type of vasopressin receptor on anterior pituitary corticotrophs? Endocrinology 1985; 116:499-502.
18. Itoh S, Yamada S, Mori T, et al. Attenuated stress-induced catecholamine release in mice lacking the vasopressin V1b receptor. Am J Physiol Endocrinol Metab 2006; 291:E147-51.
19. Wolf J P, Nguyen N U, Dumoulin G, Berthelay S. Influence of hypertonic monosaccharide infusions on the release of plasma arginine vasopressin in normal humans. Horm Metab Res 1992; 24:379-83.
20. Li J H, Jain S, McMillin S M, et al. A novel experimental strategy to assess the metabolic effects of selective activation of a G(q)-coupled receptor in hepatocytes in vivo. Endocrinology 2013; 154:3539-51.
21. Serradeil-Le Gal C, Wagnon J, Valette G, et al. Non-peptide vasopressin receptor antagonists: development of selective and orally active V1a, V2 and V1b receptor ligands. Prog Brain Res 2002; 139:197-210.
22. Serradeil-Le Gal C, Wagnon J, Simiand J, et al. Characterization of (2S,4R)-1-[5-chloro-1-[(2,4-dimethoxyphenyl)sulfonyl]-3-(2-methoxy-phenyl)-2-oxo-2,3-dihydro-1H-indol-3-yl]-4-hydroxy-N,N-dimethyl-2-pyrrolidine carboxamide (SSR149415), a selective and orally active vasopressin V1b receptor antagonist. J Pharmacol Exp Ther 2002; 300:1122-30.
23. Ryan M L, Falk D E, Fertig J B, et al. A Phase 2, Double-Blind, Placebo-Controlled Randomized Trial Assessing the Efficacy of ABT-436, a Novel V1b Receptor Antagonist, for Alcohol Dependence. Neuropsychopharmacology 2017; 42:1012-23.
24. Andres M, Trueba M, Guillon G. Pharmacological characterization of F-180: a selective human V(1a) vasopressin receptor agonist of high affinity. Br J Pharmacol 2002; 135:1828-36.
25. He X, Su F, Taccone F S, et al. A Selective V(1A) Receptor Agonist, Selepressin, Is Superior to Arginine Vasopressin and to Norepinephrine in Ovine Septic Shock. Crit Care Med 2016; 44:23-31.
26. Maybauer M O, Maybauer D M, Enkhbaatar P, et al. The selective vasopressin type 1a receptor agonist selepressin (FE 202158) blocks vascular leak in ovine severe sepsis*. Crit Care Med 2014; 42:e525-e33.
27. Wisniewski K, Galyean R, Taki H, et al. Synthesis and in vitro pharmacological profile of potent and selective peptidic V1a receptor agonists. Adv Exp Med Biol 2009; 611:507-8.

What is claimed is:
1. A method of treating fatty liver disease in a subject in need comprising administering a therapeutically effective amount of a V1b inhibitor.
2. The method of claim 1, wherein the fatty liver disease is nonalcoholic fatty liver disease.
3. The method of claim 1, wherein the fatty liver disease is alcohol related disease.

* * * * *